United States Patent
Krupp

(10) Patent No.: US 7,023,205 B1
(45) Date of Patent: Apr. 4, 2006

(54) EDDY CURRENT SENSOR CAPABLE OF SENSING THROUGH A CONDUCTIVE BARRIER

(75) Inventor: Roy S. Krupp, Mendham, NJ (US)

(73) Assignee: General Dynamics Advanced Information Systems, Inc., Arlington, VA (US)

( * ) Notice: Subject to any disclaimer, the term of this patent is extended or adjusted under 35 U.S.C. 154(b) by 225 days.

(21) Appl. No.: 09/920,427

(22) Filed: Aug. 1, 2001

Related U.S. Application Data

(60) Provisional application No. 60/222,203, filed on Aug. 1, 2000.

(51) Int. Cl.
 *G01N 27/72* (2006.01)
 *G01R 33/13* (2006.01)

(52) U.S. Cl. ...................................... 324/239; 324/240

(58) Field of Classification Search ............ 324/207.15, 324/207.25, 239, 173, 174, 228, 234–243; 73/861.78
See application file for complete search history.

(56) References Cited

U.S. PATENT DOCUMENTS

| | | | |
|---|---|---|---|
| 3,710,623 A * | 1/1973 | Boyd et al. ............... 73/861.78 |
| 3,745,392 A | 7/1973 | Phoenix et al. ............. 310/168 |
| 3,876,927 A | 4/1975 | Gee et al. ...................... 324/34 |
| 3,932,813 A | 1/1976 | Gallant ......................... 324/164 |
| 3,936,734 A | 2/1976 | Brandli et al. |
| 4,045,738 A * | 8/1977 | Buzzell ........................ 324/174 |
| 4,095,469 A | 6/1978 | Yamada et al. |
| 4,173,869 A | 11/1979 | Martin, Jr. et al. |
| 4,256,986 A * | 3/1981 | Anderson .............. 324/207.15 |
| 4,408,294 A | 10/1983 | Imam |
| 4,460,869 A | 7/1984 | Buser et al. |
| 4,468,968 A | 9/1984 | Kee |
| 4,518,917 A | 5/1985 | Oates et al. ................. 324/207 |
| 4,626,781 A * | 12/1986 | Forkel ......................... 324/174 |
| 4,647,892 A * | 3/1987 | Hewitt .................. 324/207.15 |
| 4,821,204 A | 4/1989 | Huschelrath |
| 4,841,243 A | 6/1989 | Bishop et al. .............. 324/174 |
| 4,847,556 A | 7/1989 | Langley ...................... 324/207 |
| 4,855,677 A | 8/1989 | Clark, Jr. et al. ........... 324/238 |
| 4,922,757 A * | 5/1990 | Rozelle et al. ................ 73/660 |
| 4,967,153 A | 10/1990 | Langley ...................... 324/174 |
| 4,970,670 A | 11/1990 | Twerdochlib |
| 4,987,555 A | 1/1991 | Twerdochlib ............... 364/561 |
| 5,036,274 A | 7/1991 | Seeburger .............. 324/207.16 |
| 5,063,345 A | 11/1991 | Akiyama .................... 324/173 |
| 5,097,711 A | 3/1992 | Rozelle et al. ................ 73/660 |

(Continued)

OTHER PUBLICATIONS

Dowell, Michael and Sylvester, Garrett, "Turbomachinery Prognostics and Health Management via Eddy Current Sensing: Current Developments". 1999 IEEE Aerospace Conference Proceedings, Conference held Mar. 6-13, 1999, Snowmass, Colorado.

*Primary Examiner*—Jay Patidar
(74) *Attorney, Agent, or Firm*—Howrey LLP

(57) ABSTRACT

An eddy current sensor that can be mounted on the outside of a casing for a turbine or other rotating machinery to measure characteristics of nearby, moving, electrically conductive objects through the casing. Monodirectional and omnidirectional sensors are provided. High-strength uniaxial permanent magnets generate static magnetic fields. A signal voltage is produced on a wound coil in response to a variable magnetic field caused by eddy currents in the conductive object as the conductive object passes through the stationary magnetic field. The present invention sensors are also directed to measuring characteristics of turbine blades through jet engine casings.

5 Claims, 5 Drawing Sheets

U.S. PATENT DOCUMENTS

| | | | |
|---|---|---|---|
| 5,140,264 A | 8/1992 | Metala et al. | |
| 5,206,816 A | 4/1993 | Hill et al. | |
| 5,226,731 A | 7/1993 | Allen | |
| 5,258,923 A | 11/1993 | Imam et al. | |
| 5,359,287 A | 10/1994 | Watanabe et al. | 324/207.21 |
| 5,371,462 A | 12/1994 | Hedengren et al. | |
| 5,442,285 A | 8/1995 | Zombo et al. | 324/227 |
| 5,502,999 A | 4/1996 | Seberger et al. | |
| 5,596,271 A | 1/1997 | Lowery | 324/174 |
| 5,659,246 A * | 8/1997 | Togo et al. | 324/207.15 |
| 5,670,873 A | 9/1997 | Onishi et al. | 326/174 |
| 5,698,977 A | 12/1997 | Simpson et al. | |
| 5,808,202 A | 9/1998 | Passarelli, Jr. | |
| 5,877,625 A | 3/1999 | Togo et al. | 324/174 |
| 5,914,595 A | 6/1999 | Piriou et al. | 324/220 |
| 5,942,893 A | 8/1999 | Terpay | 324/207.18 |
| 5,942,894 A | 8/1999 | Wincheski et al. | 324/220 |
| 5,963,028 A | 10/1999 | Engel et al. | 324/207.2 |
| 5,986,448 A | 11/1999 | Yada et al. | 324/173 |
| 6,094,989 A | 8/2000 | Twerdochlib | |
| 6,265,870 B1 | 7/2001 | Weischedel | 324/240 |
| 6,346,807 B1 | 2/2002 | Slates | |
| 6,594,619 B1 | 7/2003 | von Flotow | |
| 6,629,463 B1 | 10/2003 | Naudet et al. | |
| 6,657,429 B1 | 12/2003 | Goldfine et al. | |
| 6,661,222 B1 | 12/2003 | Twerdochlib | |
| 6,664,782 B1 | 12/2003 | Slates | |
| 6,692,222 B1 | 2/2004 | Prinz | |
| 6,785,635 B1 | 8/2004 | von Flotow | |
| 2002/0019708 A1 | 2/2002 | Pross | |
| 2003/0060986 A1 | 3/2003 | Flotow | |
| 2003/0071615 A1 | 4/2003 | Schlicker et al. | |
| 2004/0066188 A1 | 4/2004 | Goldfine et al. | |

* cited by examiner

EDDY CURRENT SENSOR CAPABLE OF SENSING THROUGH A CONDUCTIVE BARRIER

CROSS-REFERENCE TO RELATED APPLICATIONS

This application claims priority from provisional patent application Ser. No. 60/222,203, filed Aug. 1, 2000, by the inventor hereof, the entire disclosure of which is incorporated herein by reference.

BACKGROUND

1. Field of the Invention

This invention is related to the field of eddy current sensors. More particularly, this invention is related to an apparatus and method for measuring various parameters of moving, electrically conductive objects such as turbine blades, fan blades, and impeller, if necessary, through a casing, housing, or other barrier.

2. Description of the Problem

Eddy current sensors are known and widely used in a variety of applications to measure characteristics of moving, electrically conductive objects. A common use of eddy current sensors is in fans and turbines, where the sensors are used to measure parameters related to blade status. Such parameters can include detection of blade passing or stalling, measurement of tip clearance for individual blades, and observation of bending, torsion, vibration, cracks, and foreign object impact. The sensors generally work by creating a magnetic field through which the electrically conductive, nonmagnetic blades pass, thereby inducing an eddy current in the blades. The eddy current causes there to be a change in the magnetic field as the blade passes by the sensor, and a voltage is induced in a coil wound around a magnetically permeable core. The resulting electrical current pulses in the coil can be interpreted based on their size and shape to describe the blade characteristics.

There are two types of known eddy current sensors. The first, and most common, uses an alternating excitation current to generate an alternating magnetic field. The second uses a permanent magnet or magnets to generate a static magnetic field. Most often the magnets are shaped to form legs and resemble either a U or E, with the legs joined by a transverse flux bridge, creating a circuitous path for the magnetic field. In alternating magnetic field sensors, such as that shown in U.S. Pat. No. 5,942,893 to Terpay, the direction of the windings is selected to produce the desired relative field directions. In static field sensors, the orientation of permanent magnet poles determines the field directions, as shown in U.S. Pat. No. 3,932,813 to Gallant.

The blades to be measured are typically enclosed in a casing. Known magnetic sensor designs are either placed inside the casing or within holes in the casing so that the magnetic field does not have to pass through the casing in order to interact with the blades. Holes in the casing are undesirable because of resulting degraded mechanical performance, which is an increasing concern when there are multiple adjacent sensors as required to monitor blade vibration. Placing the sensor inside the casing is undesirable because of the expense of special modifications that must be made to create a recessed area outside of the blade path to accommodate the sensor. Both locations expose the sensors to an abusive environment that can include high temperature, corrosive gases, vibration, and blade contact. Internal sensors generate noisy signals and are expensive to build. Alternating current driven magnetic fields do not go through conductive casing materials at the high frequencies used and require substantial electronics and power to excite them and to filter and process the noisy signals generated in order to extract measurements. Such fields also generally lack the range required to function adequately outside a casing.

Known sensors, therefore, are generally inadequate to be mounted external to casings. Alternating magnetic fields do not penetrate the casing as well as static fields do. Known static field sensors, however, have inadequate strength and inappropriate geometry to generate an adequate magnetic field to penetrate casings. For example, the sensor disclosed in U.S. Pat. No. 3,932,813 is shown mounted inside a fan housing and has an E-shaped magnet with the poles quite close to each other. Its sensing coils are opposed and produce a difference signal in order to cancel noise and DC offset. This geometry limits that sensor's range severely and would be inappropriate for an external sensor.

Accordingly, there is a need to avoid the expense of internal eddy current sensors and the associated environmental and performance problems, while generating an adequate magnetic field to penetrate a casing and interact with the blades or other moving, electrically conductive parts.

SUMMARY

The present invention is directed to an eddy current sensor that can be mounted on the outside of a casing for a turbine or other rotating machinery to measure characteristics of nearby, moving, electrically conductive objects. One or more sensors generate static magnetic fields using high-strength permanent magnets, and accordingly, no excitation current is required to create the magnetic field. With the present invention, moderate-frequency eddy currents are induced in passing blades, and the resultant magnetic field disturbance is sensed and analyzed for blade status information based on the electrical current in a sensing coil. As opposed to known sensors, because the field created by the present invention is high-strength and static, it can penetrate the casing of an engine effectively, allowing the sensor to be placed outside of the casing. The returning time-varying fields from eddy currents are attenuated by the conductive casing in a predictable fashion (e.g., 4 dB/octave for 1.9 mm (76 mils) of titanium) that is compensated in subsequent digital signal processing steps.

The present invention includes two classes of sensors: monodirectional sensors and omnidirectional sensors. The present invention comprises a uniaxial permanent magnet for generating a stationary magnetic field, a winding core that is a magnetically permeable material coaxial with the magnet, and a coil wound around the winding core. The magnet is sized and shaped so that the moving conductive object can intersect the stationary magnetic field. A signal voltage can be produced on the coil in response to a variable magnetic field caused by eddy currents in the conductive object as the conductive object passes through the stationary magnetic field.

A monodirectional embodiment of the invention is provided wherein the magnet is also the winding core. The magnet is generally rectangular in cross-section, has a greatest dimension of length, and is magnetized along one of its two minor axes, resulting in a monodirectional sensor.

An omnidirectional embodiment of the invention is provided wherein the magnet is generally cylindrical and is magnetized along its longitudinal axis. The winding core may be, for example: a cylindrical rod mounted to a pole of the cylindrical magnet distal from the moving conductive object; the cylindrical magnet itself; or combination of a cylindrical rod mounted to a pole of the cylindrical magnet and the cylindrical magnet.

The sensors of the present invention are further directed to monodirectional and omnidirectional sensors for measuring characteristics of a nearby, moving, electrically conductive object through an intervening barrier of material between the sensor and the object. Some barriers cause alternating magnetic fields to provide inadequate sensor performance, for example, resulting from barriers that are too thick for alternating field to penetrate, or metal barriers that relatively high-frequency fields cannot penetrate. The longitudinal axis of the rectangular magnet of a monodirectional embodiment of the present invention is generally parallel to the proximate barrier surface. The longitudinal axis of the cylindrical magnet of an omnidirectional embodiment is generally perpendicular to the barrier surface. Each respective orientation results in a magnetic field that is generally perpendicular to the barrier surface.

The present invention sensors are yet further directed to measuring characteristics of turbine blades through jet engine casings. Examples of permanent type magnets include rare earth, ceramic, or alnico, all of which are high-strength and generate a large magnetic field through which the blades pass. Methods for sensing blade characteristics are also provided according to the present invention.

Features and advantages of the present invention will become more apparent in light of the following detailed description of some embodiments thereof, as illustrated in the accompanying figures. As will be realized, the invention is capable of modifications in various respects, all without departing from the invention. Accordingly, the drawings and the description are to be regarded as illustrative in nature, and not as restrictive.

DETAILED DESCRIPTION OF ONE OR MORE EMBODIMENTS

Figure 1:
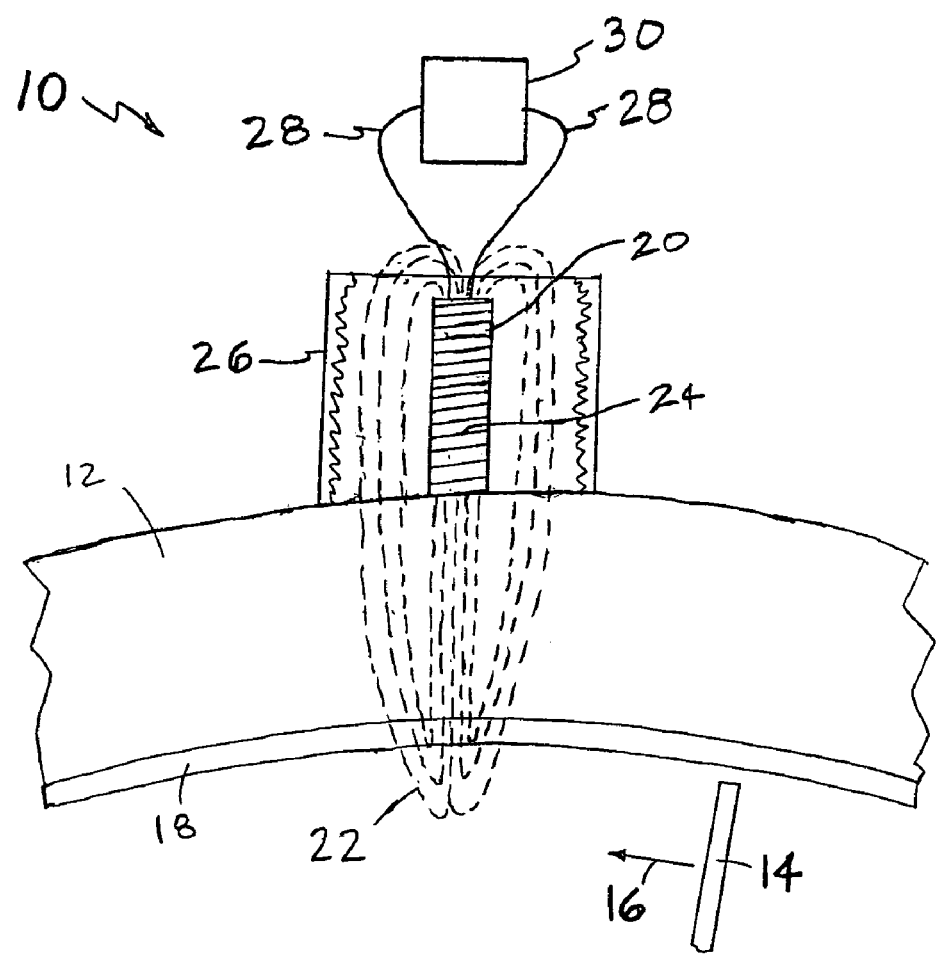
FIG. 1 is a schematic elevation view of the present invention in one application.

The present invention is directed to an external eddy current sensor that uses a permanent magnet to generate a static magnetic field. FIG. 1 shows one configuration for use of the present invention, with sensor assembly 10 mounted on a nonferrous engine casing 12 with a blade 14 rotating 16. A thin nonmagnetic, nonconductive material layer 18 is shown that is normally used in gas turbines for preventing damage to the blade as the result of accidental contact with the casing 12. The sensor 20 itself includes a very strong magnet that generates a large static magnetic field 22, and wire sensing coils 24. A housing 26, shown cut away to expose the sensor 20, may encase the sensor 20.

It should be understood that the scale of FIG. 1 and similar figures is quite distorted since the casing 12 is typically 1.2 to 2.5 mm (50 to 100 mils) thick, while sensor 20 dimensions are in the magnitude of 6 to 25 mm (¼ to 1 inch). In addition, specific terms such as "casing" and "blades" are used for the purpose of describing the invention and its use, but should not be considered to limit the invention's scope. For example, although the term casing is used herein to describe material between the sensor and the component being detected, it should be understood that the casing could be a housing, a sheet of material, or any similar barrier, and that the thickness of such materials may vary.

Figure 2:
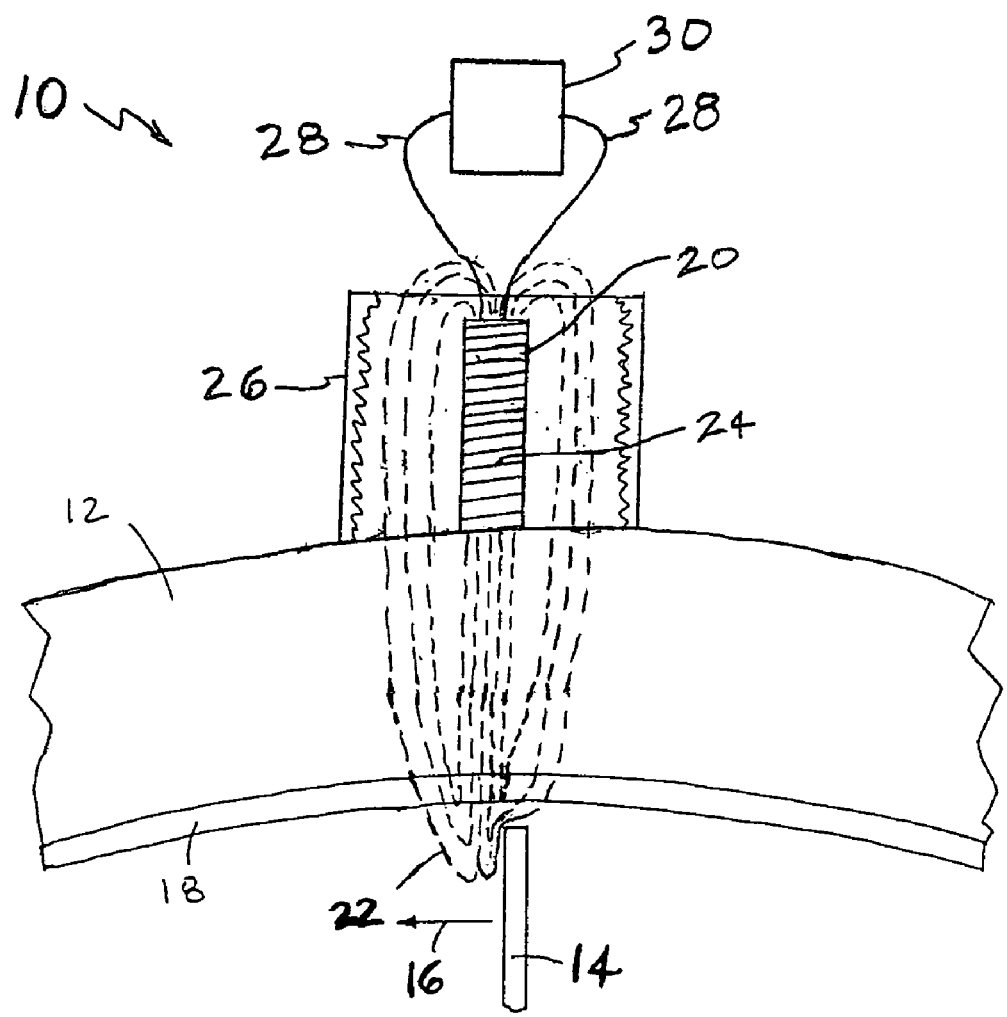
FIG. 2 is the same elevation view as FIG. 1, after time has elapsed.

The magnet in the sensor 20 generates a large static magnetic field 22, preferably in the magnitude of 12 to 25 mm (½ to 1-inch) range, through which blades 14 pass at high speed. This range is usually adequate, but a larger range generally may be achieved by use of bigger sensors. The motion of the blades 14 through the magnetic field 22 generates temporary eddy currents in the blade tips, which in turn generate moving magnetic fields that disturb the static magnetic field 22, as shown in FIG. 2. The sensing coils 24 for detecting the moving fields are wound around either the original magnet, associated shapes of high permeability material, or both, which as applicable are individually or in combination referred to as a winding core. Orientation of the sensing coils 24 varies in some embodiments of the invention from that shown in FIG. 1. The moving magnetic fields produce electrical pulses in the coils 24 and pass through the coil 24 wire ends 28 and through a known signal processor 30. The size, shape, and timing of the pulses yield information about the blades 14.

In passing through the casing 12 to sensing coils 24, the moving magnetic fields are partially attenuated and delayed, but at the frequencies involved (tens of KHz) this effect can be compensated by standard signal processing methods known to one of ordinary skill in the art. In fact, the frequency dependent attenuation tends to moderate the dependence of pulse size on blade 14 tip speed. The pulses are converted in the processor 30 to digital samples at high speed, screened for peaks, zero crossings, and other useful features, and then processed to extract blade information.

Figure 3:
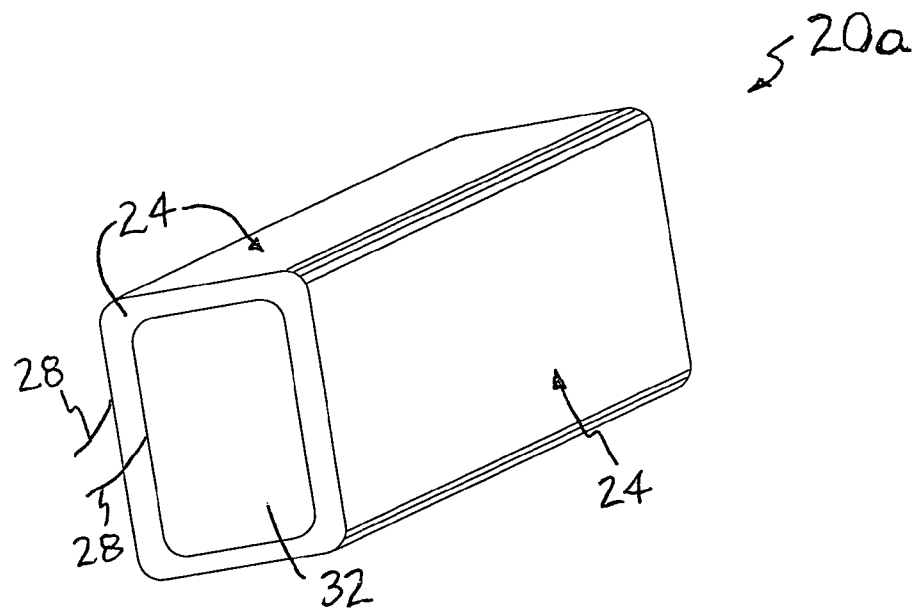
FIG. 3 is a perspective view of one embodiment of the present invention.
Figure 4:
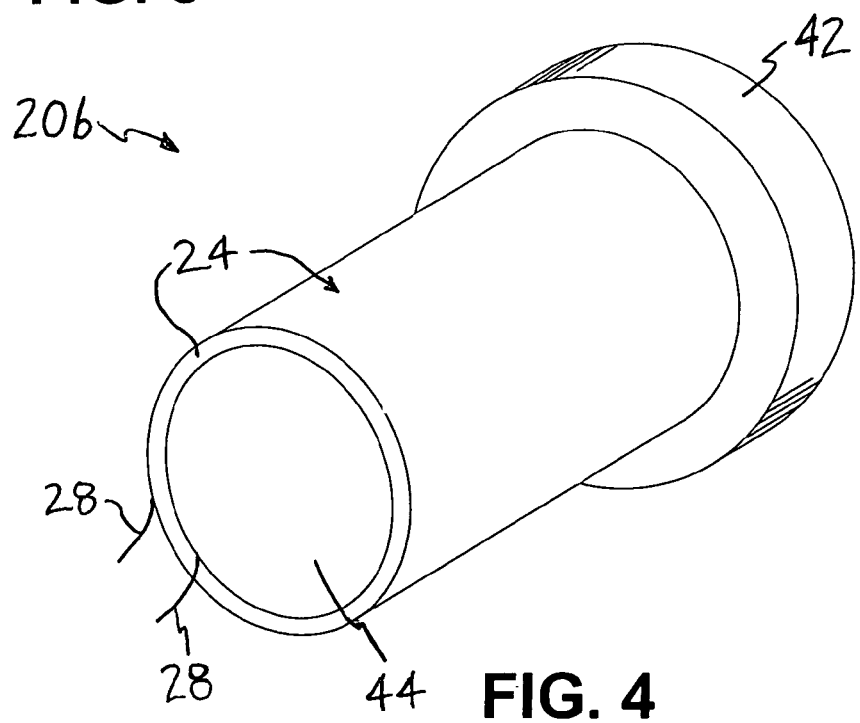
FIG. 4 is a perspective view of another embodiment of the present invention.

The present invention includes two classes of sensors that can be mounted outside of a casing of, for example, a jet engine. Embodiments of each of these classes of sensors are shown in FIGS. 3 and 4. Monodirectional sensors 20a (FIG. 3) must be aligned on the casing to take account of the angle of tilt and direction of motion of the turbine blades 14. Omnidirectional sensors 20b (FIG. 4) are symmetric about an axis normal to the casing and need not be aligned with the blade 14.

The geometry of the sensor is important to establishing the range of the stationary magnetic field used to excite eddy currents. The external sensor may be, for example, as much as 12 mm (½-inch) or more away from the blades. Typically, the field range varies with the dimensions of the magnet. Specifically, for a circular magnet that is thin along the direction of magnetization (the typical case for rare earth types) with a radius of R, length L with L being much less than R, and residual induction of the material Br, the field/(magnet volume) at the centerline of the magnet a distance X from the surface of a pole is approximately:

Field/Volume=$Br/2\pi(R^2+X^2)^{3/2}$.

Thus the field begins to decrease rapidly when X is comparable to R (its range) and eventually decays as the inverse cube of X/R, like any dipole field.

The monodirectional sensor 20a in FIG. 3 comprises a rectangular bar permanent magnet 32 with a sensing coil 24 wound around it. The rectangular bar magnet 32 generally has a greatest dimension of length, and its central longitudinal, or major, axis is generally parallel to the proximate casing 12 surface. The magnet 32 is magnetized along one of its short, or minor, axes (perpendicular to the longitudinal axis and generally parallel to respective sides of the magnet 32) and the resulting sensor 20a is highly directional. In general, the range of this type of sensor may be estimated as approximately the square root of the area of its largest face extending perpendicularly from the casing 12.

The wire of the coil 24 may be any electrically conductive wire with a coating of insulation as commonly used in electromagnets and other electronics, for example, 36 gauge copper wire. The insulation on the wire is commonly nylon, and double thickness nylon is available that helps assure integrity. An additional insulator such as liquid acetate compound may be applied between layers of wire winding, but tape made from polytetrafluoroethylene (PTFE, marketed as TEFLON, a registered trademark of E.I. duPont de Nemours and Company) is preferable. The scope of the invention is not intended to be limited by the materials or dimensions listed herein, but may be carried out using any materials and dimensions that allow the construction and operation of the sensor as readily known by one of ordinary skill in the art.

Figure 5:
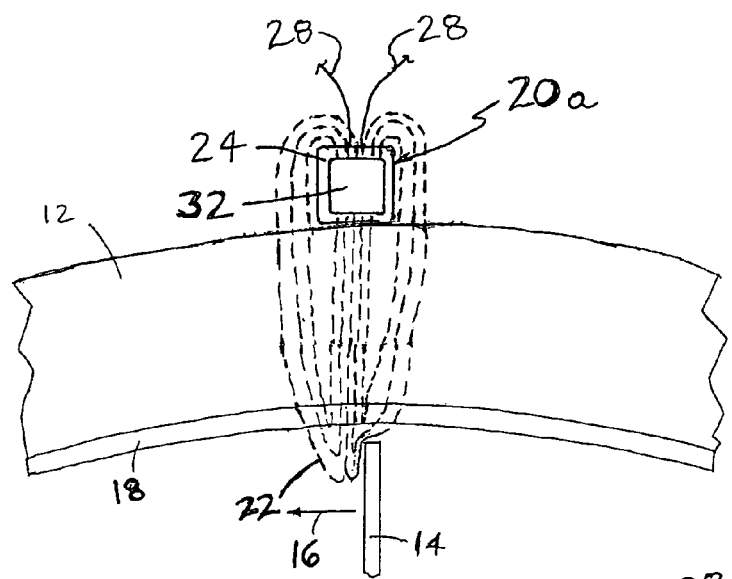
FIG. 5 is a schematic elevation view of the embodiment of FIG. 3 in an application.

FIG. 5 shows an application of a monodirectional sensor 20a. The magnetic field is perpendicular to the casing 12, and a central axis through the coil 24 is parallel to the casing 12.

The omnidirectional sensor 20b in FIG. 4 is axisymmetric, and comprises a cylindrical magnet 42, a cylindrical magnetically permeable rod 44, and a coil 24 wound around the rod 44. The rod 44 is preferably a ferrite material, but may be a magnet itself. The magnet 42 can be attached to the rod 44 using an adhesive suitable for the application. The rod 44 moves one pole of the magnet 42 farther from the other to increase the field range, and is also a convenient place to wind the sensing coil 24. In general, the range of this type of sensor 20b may be estimated to be approximately the same as the distance between the magnet 42 surface proximate to the casing and the distal end of the rod 44. The wire of the coil 24 is similar to that described for the monodirectional sensor 20a.

Figure 6:
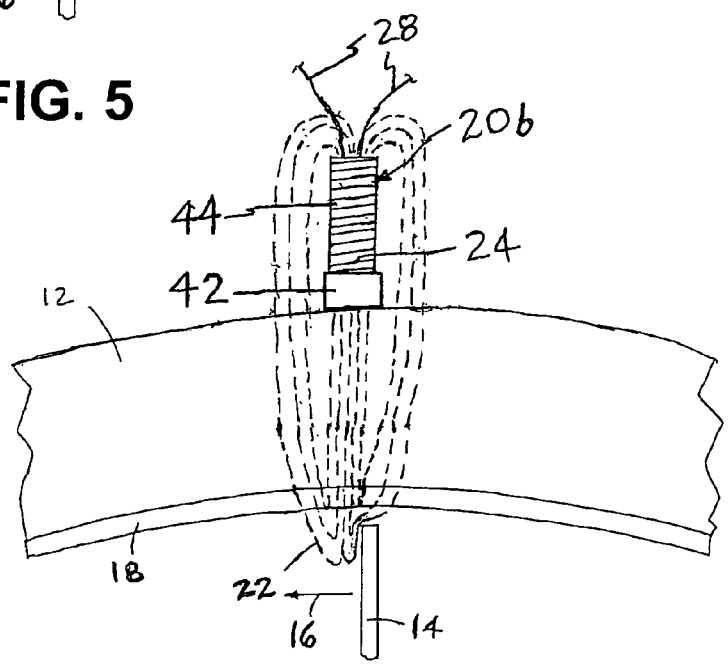
FIG. 6 is a schematic elevation view of the embodiment of FIG. 4 in an application.

FIG. 6 shows an application of an omnidirectional sensor 20b. The magnetic field 22 and a central axis through the coil 24 are each perpendicular to the casing 12.

Figure 7:
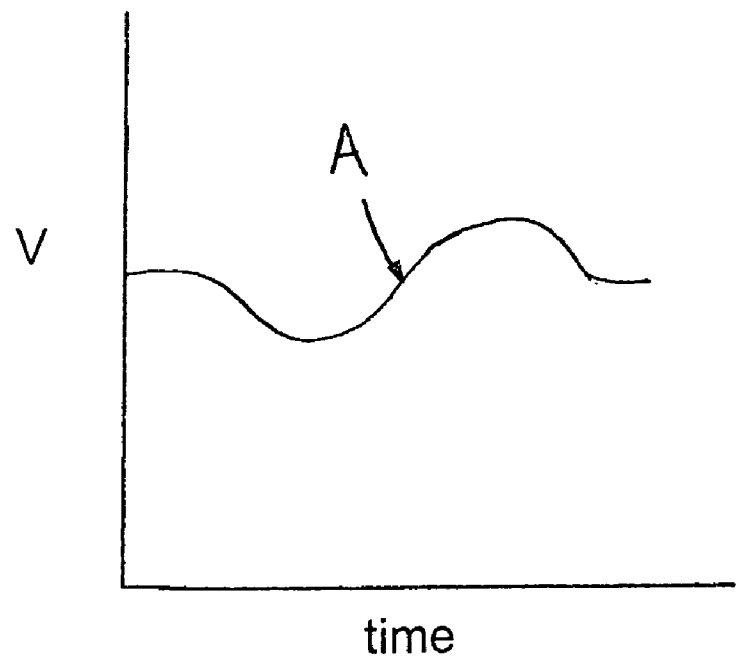
FIG. 7 is an exemplary waveform of a signal generated by the embodiment of the present invention shown in FIGS. 3 and 5.
Figure 8:
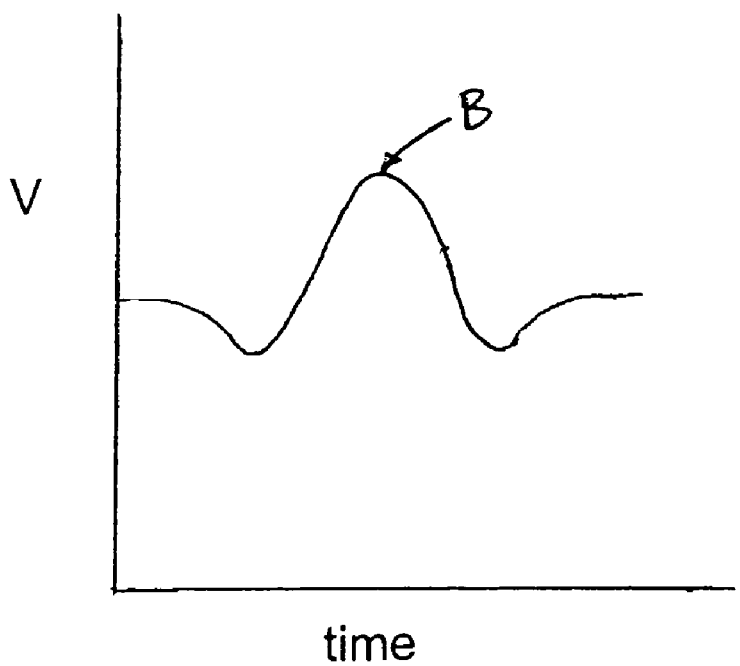
FIG. 8 is an exemplary waveform of a signal generated by the embodiment of the present invention shown in FIGS. 4 and 6.

The main difference between the two embodiments 20a, 20b is the type of pulse shapes produced, depicted in general with volts plotted versus time in FIGS. 7 and 8. Monodirectional sensors produce S-shaped pulses as shown in FIG. 7, with a zero-crossing at point A approximately at the time of closest approach of the blade.

Omnidirectional sensors exhibit a tall central peak at closest approach as shown in FIG. 8 at point B. Thus measurement capabilities and signal processing requirements differ somewhat in the two cases. Other geometries are possible, such as several sensors sharing a single strong magnet to reduce spacing between them. The selection of geometry varies with the desired application; for example, the choice may be driven by the value of fitting multiple sensors close together in one housing to reduce cost, monitor several points along the chord of each blade, or measure blade speed based on time of flight between sensors.

Testing was performed on the two embodiments 20a, 20b shown in FIGS. 3 and 4 respectively. The test configurations resembled FIGS. 5 and 6 except the sensors were mounted behind a flat sheet of 1.9 mm (76 mil) grade 2 titanium instead of a curved sheet (casing 12) shown in the figures. A tested monodirectional sensor 20a had magnetic bar 32 dimensions approximately as follows: 19 mm (¾-inch) length, and a square cross-section of 6 mm (¼-inch). A tested omnidirectional sensor 20b had dimensions approximately as follows: magnet 42 diameter of 13 mm (½-inch) and length of 6 mm (¼-inch); rod 44 diameter of 6 mm (¼-inch) and length of 17 mm (¹¹⁄₁₆-inch).

Typical measured pulses in the tests were a few volts into 210 ohms at 10,000 RPM, with a tip clearance of 1.5 mm (61 mils) plus the 1.9 mm (76 mil) titanium sheet to simulate a jet engine casing. Associated sensor electronics were not used; output of coils went straight to recording devices for later analysis. Rare earth magnets were used in the tested embodiments.

Magnet material selection varies with the application. Rare earth magnets are the most powerful permanent magnets, and include those made of Nd—Fe—B (Neodymium-Iron-Boron). The testing was performed with Nd—Fe—B magnets, which are readily obtained, inexpensive, and the highest strength. Nd—Fe—B magnets, however, have a poor temperature range and are apt to corrode. Samarium-Cobalt (Sm—Co) magnets are weaker, have somewhat better temperature limits, and do not corrode, but cost more and are harder to obtain. Both of these magnets are valued in motors and loudspeakers for their high coercive force, but this is unlikely to be an issue in a use such as that in FIGS. 1 and 2 since in general no other strong magnetic field or current is present. Alnico (Aluminum-Nickel-Cobalt) magnets have poor coercive force and are difficult to machine, but have a superior temperature range that makes them the best choice for jet engine applications. Since pulse signal size scales proportionally to field strength, strong excitation magnets are desirable, but depending on the application any of the above types may be suitable.

External sensors can be thermally and mechanically isolated from environmental stress, thereby extending their useful lives. They are inexpensive and easy to install; a few can share a single housing to monitor blade motion and reduce the cost of connectors and mounting. They are stable, passive devices that generate pulses from the energy of the blade motion alone, that with appropriate cabling and shielding and a low impedance load produce clean signals with little noise and no need for an excitation current to create the magnetic field. No holes in casings or expensive modifications to accommodate sensors inside the casings are required; simple silicone-based adhesive may be adequate for temporary installations.

Specific embodiments of an invention are described herein. One of ordinary skill in the electronics arts will quickly recognize that the invention has other applications in other environments. In fact, many embodiments and implementations are possible. For example, although there are substantial benefits available by use of the invention to sense eddy currents through a barrier, the present invention can also be used when there are no intervening barriers. The following claims are in no way intended to limit the scope of the invention to the specific embodiments described above.

What is claimed is:

1. An eddy current sensor for measuring characteristics of a nearby, moving, electrically conductive object with an intervening barrier of material between the sensors and the object, the sensor comprising:
   a uniaxial permanent magnet for generating a stationary magnetic field, the magnet being mounted proximate and external to the barrier and sized and shaped so that the stationary magnetic field penetrates through the barrier and can be intersected by the moving conductive object; and
   a coil wound around the magnet so that a signal voltage can be produced on the coil in response to a variable magnetic field caused by eddy currents in the conductive object as the conductive object passes through the stationary magnetic field;
   wherein the magnet includes a first dimension along a longitudinal central major axis generally parallel to the proximate surface of the barrier, a second dimension along a second minor axis, and third dimension along a third minor axis, the first dimension being the greatest, and wherein the magnet is magnetized along one of the second minor axis and the third minor axis, whereby the sensor is monodirectional.

2. The eddy current sensor as recited in claim 1, wherein the magnet is generally rectangular in cross-section.

3. An eddy current sensor for measuring characteristics of moving turbine blades of a jet engine having a casing, through which the sensor measures the blade characteristics, the sensor comprising:
   a uniaxial permanent magnet for generating a stationary magnetic field, the magnet being mounted proximate and external to the casing and sized so that the stationary magnetic field penetrates through the casing and can be intersected by a portion of the blade, wherein the magnet includes a generally rectangular cross-section, a first dimension along a longitudinal central major axis generally parallel to the proximate surface of the casing, a second dimension along a second minor axis, and third dimension along a third minor axis, the first dimension being the greatest, and the magnet is magnetized substantially along one of the second minor axis and the third minor axis; and
   a coil wound around the magnet so that a signal voltage can be produced on the coil in response to a variable magnetic field caused by eddy currents in the blade as the blade passes through the stationary magnetic field, whereby the sensor is substantially monodirectional.

4. The eddy current sensor as recited in claim 3, wherein the magnet material is selected from the group consisting of Neodymium-Iron-Boron, Samarium-Cobalt, and Aluminum-Nickel-Cobalt.

5. A method of measuring characteristics of moving turbine blades of a jet engine having a casing, through which blade characteristics are sensed, comprising the steps of:
   generating a stationary magnetic field by using a substantially uniaxial permanent magnet, the magnet being mounted proximate and external to the casing and sized so that the stationary magnetic field penetrates through the casing and can be intersected by a portion of the blade, the magnet includes a generally rectangular cross-section, a first dimension along a longitudinal central major axis generally parallel to the proximate surface of the casing, a second dimension along a second minor axis, and third dimension along a third minor axis, the first dimension being the greatest, and the magnet being magnetized substantially along one of the second minor axis and the third minor axis;
   producing a signal voltage on a coil wound around the magnet in response to a variable magnetic field caused by eddy currents in the blade as the blade passes through the stationary magnetic field; and
   measuring the signal voltage.

\* \* \* \* \*